United States Patent [19]
Grandis

[11] Patent Number: 6,063,586
[45] Date of Patent: May 16, 2000

[54] DIAGNOSTIC PROTOCOL

[75] Inventor: Jennifer Rubin Grandis, Pittsburgh, Pa.

[73] Assignee: Eye & Ear Foundation, Oakmont, Pa.

[21] Appl. No.: 09/018,796

[22] Filed: Feb. 4, 1998

Related U.S. Application Data

[63] Continuation of application No. 08/922,873, Sep. 3, 1997.

[51] Int. Cl.$^7$ .......................... A61K 39/395; G01N 33/53
[52] U.S. Cl. .......................... 435/7.23; 435/7.2; 435/335; 435/344; 530/388.23; 530/388.8; 530/389.7; 530/389.2; 424/145.1; 424/155.1; 424/174.1
[58] Field of Search .............................. 424/130.1, 138.1, 424/141.1, 142.1, 143.1, 145.1, 155.1, 174.1; 435/4, 7.1, 7.21, 7.8, 326, 7.23, 7.2, 335, 344; 436/512, 548; 530/387.1, 388.1, 388.22, 388.8, 389.7, 389.2

[56] References Cited

U.S. PATENT DOCUMENTS 5,674,753  10/1997  Harvey et al. ........................... 436/501

OTHER PUBLICATIONS

Iihara et al., Cancer vol. 71 No. 10, pp. 2902–2909, May 15, 1993.
Gasparini et. al., Breast Cancer Res. and Treat. vol. 29, pp. 59–71, Jan. 1, 1994.
Toi et. al., Breast Cancer Res. and Treat., vol. 29, pp. 51–58, Jan. 1, 1994.
Kimball, J.M., Introduction to Immunology, Macmillan Publishing Co., Inc., 866 Third Ave., New York, New York, 1983.

*Primary Examiner*—Julie Burke
*Attorney, Agent, or Firm*—Webb Ziesenheim Logsdon Orkin & Hanson, P.C.

[57] ABSTRACT

A cancer prognostic having particular utility in the prognosis of head and neck squamous cell cancer, in which the expression levels of either or both of Transforming Growth Factor Alpha (TGF-α) or Epidermal Growth Factor Receptor (EGFR) are assayed directly from a sample of tumor tissue. The expression level once quantitated is normalized as to standard, and the standardized expression level is compared to the prognostic threshold of about 83% of standard for TGF-α or of about 23% of standard for EGFR, or the corresponding upper threshold of the "low" tertile regardless of how calculated. Virtually all if not all patients demonstrating this low expression level survive at least five years after initial diagnosis, assuming completion of treatment with standard surgical tumor excision and radiation protocols for squamous cell head and neck cancer. Whether an individual patient's expression levels of TGF-α and EGFR fall inside or outside of this category signifies whether the patient is in a good or poor prognostic category, respectively, which in turn guides appropriate choice of therapy.

8 Claims, 8 Drawing Sheets

Clinicopathologic Charecteristics According to TGF-α/EGFR Tumor Levels
in 91 Patients Undergoing Resection for Head and Neck Squamous Cell Carcinoma

| % of Standard | TGF-α | | | | EGFR | | | |
|---|---|---|---|---|---|---|---|---|
| | Low 0-83.0 | Medium 84.0-181.9 | High 182.0+ | Test Of Independence p Value | Low 0-22.9 | Medium 30.0-99.9 | High 100.0+ | Test Of Independence p Value |
| No. Of Patients % | 30(33) | 31(34) | 30(33) | — | 30(33) | 30(33) | 31(34) | — |
| Sex | | | | 0.772 | | | | 0.772 |
| M | 23(35) | 21(32) | 21(32) | NS | 21(32) | 23(36) | 21(32) | NS |
| F | 7(27) | 10(38) | 9(35) | | 9(35) | 7(27) | 10(38) | |
| Age | | | | 0.354 | | | | 0.751 |
| <65 | 11(26) | 17(40) | 15(34) | NS | 16(37) | 13(30) | 14(33) | NS |
| 65+ | 19(40) | 14(29) | 15(31) | | 14(30) | 17(35) | 17(35) | |
| Tumor Site | | | | 0.128 | | | | 0.158 |
| Oral Cavity | 9(35) | 6(23) | 11(42) | NS | 6(24) | 10(38) | 10(38) | NS |
| Oropharynx | 5(42) | 4(33) | 3(25) | | 5(42) | 4(33) | 3(25) | |
| Hypopharynx | 2(12) | 6(35) | 9(53) | | 2(12) | 6(35) | 9(53) | |
| Larynx | 14(39) | 15(42) | 7(19) | | 17(47) | 10(28) | 9(25) | |
| T Stage | | | | 0.493 | | | | 0.607 |
| T1 | 5(36) | 5(36) | 4(28) | NS | 7(50) | 4(29) | 3(21) | NS |
| T1 | 11(33) | 9(28) | 13(39) | | 10(31) | 11(33) | 12(36) | |
| T3 | 10(43) | 6(27) | 7(30) | | 9(39) | 6(26) | 8(35) | |
| T4 | 4(19) | 11(52) | 6(29) | | 4(19) | 9(43) | 8(38) | |
| N Stage | | | | 0.117 | | | | 0.073 |
| N0 | 18(37) | 19(39) | 12(24) | NS | 21(43) | 12(24) | 16(33) | NS |
| N1 | 7(47) | 4(27) | 4(26) | | 5(33) | 4(27) | 6(40) | |
| N2 | 5(18) | 8(30) | 14(52) | | 4(15) | 14(52) | 9(33) | |
| Differentiation | | | | 0.404 | | | | 0.111 |
| Well | 12(48) | 6(24) | 7(28) | NS | 13(52) | 7(28) | 5(20) | NS |
| Moderate | 15(28) | 20(38) | 17(34) | | 14(27) | 16(31) | 22(42) | |
| Poor | 3(21) | 3(36) | 6(43) | | 3(21) | 7(50) | 4(29) | |

FIG. 1

Association of Potential Prognostic Factors and Disease Free Survival

| Prognostic Factor | Subgroup | Recurrent Disease Number at Risk | Probability of Surviving 2 Years | Lower 95% Confidence Bound + (years) | Log Rank p | Adjusted p |
|---|---|---|---|---|---|---|
| All Patients | — | 42/91 | .69 | 2.5 | — | — |
| Gender | Male | 27/65 | .70 | 2.5 | .3183 | 1.0 |
|  | Female | 15/26 | .88 | 2.1 | NS | NS |
| Age | <65 | 19/43 | .66 | 2.5 | .8644 | 1.0 |
|  | 65+ | 23/48 | .73 | 2.3 | NS | NS |
| Site | oral cavity | 16/26 | .51 | 1.2 | 0.414 | .2484 |
|  | oropharynx | 7/12 | .67 | 2.0 |  | NS |
|  | hypopharynx | 9/17 | .68 | 1.7 |  |  |
|  | larynx | 10/36 | .84 | 4.5 |  |  |
| Grade | well diff. | 10/25 | .70 | 2.1 | .6720 | 1.0 |
|  | mod. diff. | 26/52 | .72 | 2.5 | NS | NS |
|  | poorly diff. | 6/14 | .60 | 1.3 |  |  |
| T Stage | 1 | 5/14 | .77 | 2.1 | .2470 | .9880 |
|  | 2 | 17/33 | .58 | 1.7 | NS | NS |
|  | 3 | 9/23 | .91 | 3.0 |  |  |
|  | 4 | 11/21 | .58 | 0.6 |  |  |
| N Stage | 0 | 19/49 | .74 | 2.5 | .1119 | .5595 |
|  | 1 | 8/15 | .79 | 2.3 | NS | NS |
|  | 2 | 15/27 | .55 | 1.3 |  |  |
| TGF-α (% of Standard) | low | 5/30 | .93 | - | .0001 | .0001 |
|  | medium | 15/31 | .64 | 2.0 |  |  |
|  | high | 22/30 | .50 | 1.2 |  |  |
| EGFR (% of Standard) | low | 5/30 | .90 | 5.2 | .0001 | .0001 |
|  | medium | 11/30 | .70 | 2.5 |  |  |
|  | high | 26/31 | .49 | 1.2 |  |  |

+ This is the lower 95% confidence bound for the median survival. In most cases median survival has not been reached.

FIG. 2

Association of Potential Prognostic Factors and Overall Cause-Specific Survival

| Prognostic Factor | Subgroup | Deaths from Disease Number at Risk | Probability of Surviving 2 Years | Lower 95% Confidence Bound + (years) | Log Rank p | Adjusted p |
|---|---|---|---|---|---|---|
| All Patients | — | 32/91 | .88 | 4.5 | — | — |
| Gender | Male<br>Female | 22/65<br>10/26 | .80<br>.88 | 4.2<br>3.2 | .7501<br>NS | .7501<br>NS |
| Age | <65<br>65+ | 17/43<br>15/48 | .78<br>.86 | 3.1<br>4.2 | .3222<br>NS | .6444<br>NS |
| Site | oral cavity<br>oropharynx<br>hypopharynx<br>larynx | 10/26<br>6/12<br>9/17<br>7/36 | .80<br>.83<br>.69<br>.91 | 2.1<br>2.5<br>1.8<br>— | .0927<br>NS | .3708<br>NS |
| Grade | well diff.<br>mod. diff.<br>poorly diff. | 5/25<br>20/52<br>7/14 | .92<br>.82<br>.69 | —<br>3.3<br>2.0 | .1089<br>NS | .3708<br>NS |
| T Stage | 1<br>2<br>3<br>4 | 2/14<br>13/33<br>7/23<br>10/21 | 1.0<br>.81<br>.95<br>.59 | —<br>3.2<br>4.5<br>0.8 | .0656<br>NS | .2825<br>NS |
| N Stage | 0<br>1<br>2 | 11/49<br>6/15<br>15/27 | .92<br>.86<br>.64 | —<br>3.4<br>1.4 | .0012 | .0072<br>NS |
| TGF-α (% of Standard) | low<br>medium<br>high | 0/30<br>12/31<br>20/30 | 1.0<br>.82<br>.64 | —<br>2.8<br>2.0 | .0001 | .0001<br>NS |
| EGFR (% of Standard) | low<br>medium<br>high | 0/30<br>10/30<br>22/31 | 1.0<br>.81<br>.66 | —<br>4.5<br>1.8 | .0001 | .0001<br>NS |

+ This is the lower 95% confidence bound for the median survival. In most cases median survival has not been reached.

FIG. 3

DIAGNOSTIC PROTOCOL

CROSS REFERENCE TO RELATED APPLICATION

This application is a continuation of copending U.S. application Ser. No. 08/922,873, filed Sep. 3, 1997, entitled "Diagnostic Protocol."

FIELD OF THE INVENTION

The present invention relates to a diagnostic protocol incorporating a medical prognostic; the prognostic is designed to predict the survival of a given patient, in whom malignancy has been previously diagnosed.

BACKGROUND OF THE INVENTION

The field of pathology is evolving so as to embrace two disciplines, one of which is subsumed into the other: diagnosis and prognosis. Each is a medical discipline in which biochemistry and molecular biology play increasingly important roles, allowing innovations in traditional diagnosis as well as reliable protocols for prospective outcome prediction. If a diagnostic test or assay, or "diagnostic," provides specific information regarding the nature of a disease, a "prognostic" test or assay provides specific information regarding the outcome of that disease—but within the conceptual confines of the original diagnostic. Properly developed prognostics allow a determination to be made in advance, with statistically significant and surprising accuracy and precision, whether a given drug or active agent, or therapeutic protocol including surgery or other treatments, will be effective to inhibit or to overcome the disease or condition in question.

In a very real sense, prognostics give a wider scope of benefit than traditional diagnostics do, even though they fall within the diagnostic field in general. Before the advent of the field of prognostics, various therapies had to be attempted sequentially based upon general guidelines developed from overall patient population data, but in many cases these general guidelines had disappointing predictive value with respect to any given patient or any given treatment. Against this backdrop, it can be seen that a prognostic can yield not only scientific and medical value but also both a heretofore-elusive humanitarian advantage (quality of life) as well as significant economic benefit (cost effectiveness). With a prognostic, for example, a given patient need not endure a given treatment simply to ascertain whether that treatment is likely to be effective. A properly designed prognostic gives a health care provider information about risk category and likelihood of survival, which in turn assists in determining appropriate therapy. It is easy to appreciate the particular utility of a prognostic in the challenging area of cancer treatment, where the benefit of a patient's not having to endure unnecessary treatment may be the greatest for any disease.

Cost savings also become significant when medical practitioners are provided with a tool by which to predict, for a given patient, whether a given therapy will be effective—because therapies unlikely to be effective are generally passed over at the outset. (Alternatively, the prognostic's predictive utility may appropriately identify patients for inclusion in the prospective investigation of novel treatments.) When therapies unlikely to be effective are skipped altogether, the costs (and waste) involved in the failed therapy are also avoided. Neither the cost nor the health benefit of avoiding likely-to-be-futile therapies should be underestimated. The improvement in morale in any patient who knows his chosen therapy is predictably effective as to him or her individually itself contributes to the successful therapy in a manner analogous to the placebo effect.

In general, the best prognostics are those in which the particular biochemistry or molecular biology of biopsied tissue—or, alternatively, of blood or body fluids—can be assayed and quantitated to yield an objective outcome likelihood. Such biochemical "markers" might be anything, including but not limited to catabolytes, anabolytes, enzymes, hormones, other expressed peptides or proteins, distinct saccharides, or any other distinctive biomolecule. As a design consideration, the theoretically best biochemical marker for a prognostic would be one or more uniquely expressed peptides or proteins, because these could be readily identified (and quantitated) by corresponding monoclonal antibodies. The ideal cancer prognostic would therefore involve the identification of a critical threshold expression level for one or more unique peptides or proteins having prognostic significance. Such an assay could be performed with existing laboratory reagents and equipment, using standard monoclonal antibodies and optical-counting quantitation techniques, and would therefore be inexpensive as well as accurate and precise. Because the assay would be undertaken to ascertain expression levels in a given patient, the results would have prognostic value specific to that patient.

SUMMARY OF THE INVENTION

In order to meet this need for optimal, risk-adjusted clinical decisions, the present invention is a cancer prognostic having particular utility in the prognosis of head and neck squamous cell cancer, in which the expression levels of either or both of Transforming Growth Factor Alpha (TGF-$\alpha$) or Epidermal Growth Factor Receptor (EGFR) are assayed directly and separately from a sample of tumor tissue. The expression level once quantitated is normalized as to standard, and the standardized expression level is compared to the prognostic threshold of about 83% of standard for TGF-$\alpha$ or of about 23% of standard for EGFR, or the corresponding upper threshold of the "low" tertile regardless of how calculated. Virtually "all" (if not absolutely all) patients demonstrating such low expression level survive at least five years after initial diagnosis, assuming completion of treatment with standard surgical tumor excision and radiation protocols for squamous cell head and neck cancer. Whether an individual patient's expression levels of TGF-$\alpha$ and EGFR fall inside or outside of this category signifies whether the patient is in a good or poor prognostic category, respectively, which in turn guides appropriate choice of therapy.

BRIEF DESCRIPTION OF THE FIGURES

FIG. 1 is a Table illustrating TGF-$\alpha$ and EGFR expression levels in a study of 91 patients.

FIG. 2 is a Table illustrating association of potential prognostic factors and disease free survival in the same study.

FIG. 3 is a Table illustrating association of potential prognostic factors and overall cause-specific survival in the same study.

DETAILED DESCRIPTION OF THE INVENTION

Figure 4:
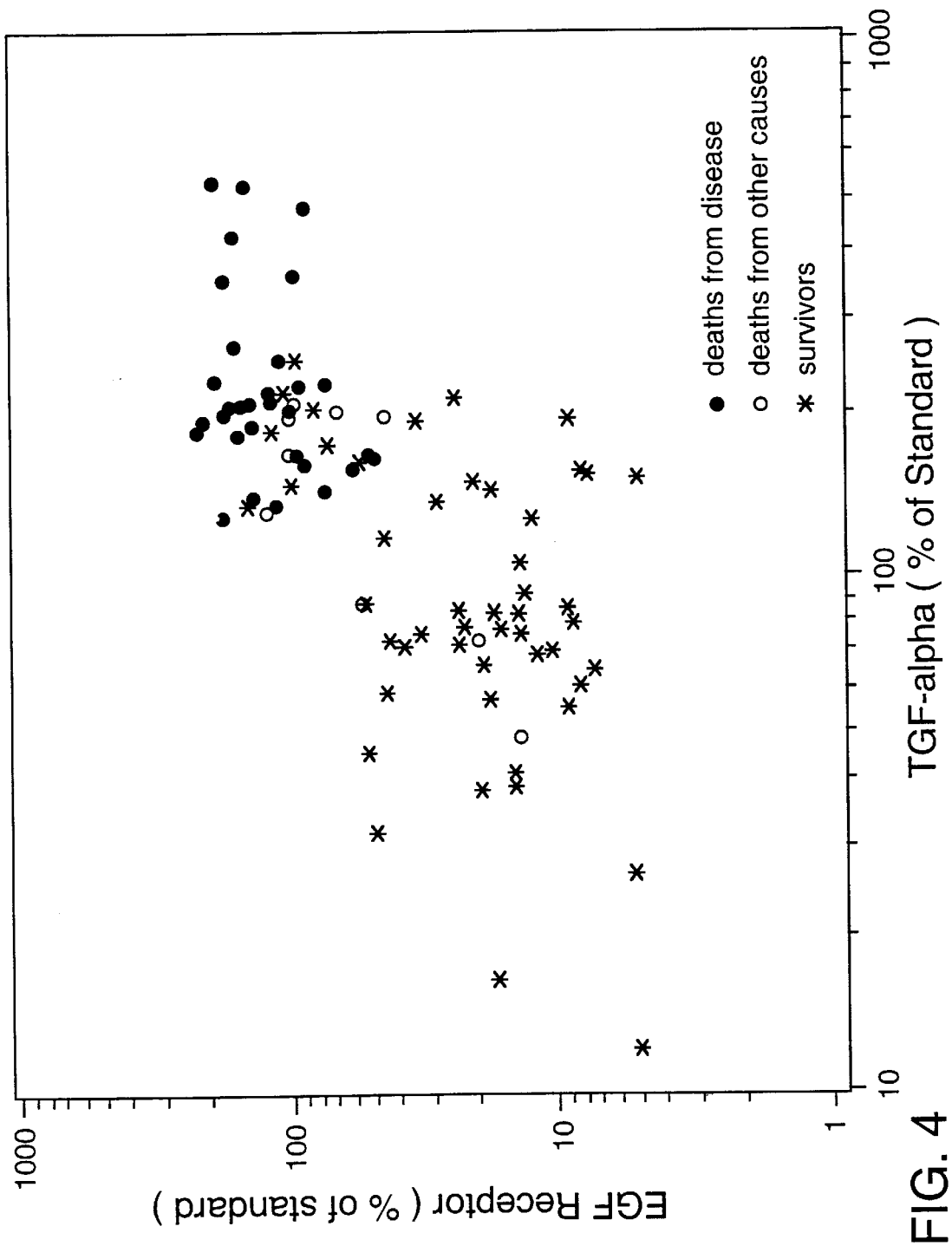
FIG. 4 is a graph showing individual patients plotted against their elevated TGF-$\alpha$ and EGFR levels.

Transforming Growth Factor Alpha (TGF-α) is a polypeptide of 50 amino acids. It was first isolated from a retrovirus-transformed mouse cell line and subsequently was identified in human tumor cells, in early rat embryo cells and in cell cultures from the human pituitary gland. Transforming Growth Factor Alpha (TGF-α) appears to be closely related to Epidermal Growth Factor (EGF), both structurally and functionally, and both bind to the same receptor, i.e., Epidermal Growth Factor Receptor (EGFR). Study of TGF-α has heretofore concentrated on its presence as a cancer marker and the likely value of TGF-α antagonists as therapeutic tools, not on quantitative expression levels of TGF-α or their potential prognostic significance.

Head and neck squamous cell carcinoma is an epithelial malignancy arising in the mucosa of the upper aerodigestive tract. Potential anatomic sites affected include the oral cavity, oropharynx, hypopharynx and larynx. Approximately half of the patients diagnosed have traditionally been cured of their initial tumor. Factors such as age, sex, tumor site, "TNM" stage and histologic grade have generally been relied on to assist in guiding treatment decisions but are not in fact useful predictors of outcome. Nodal stage assessment of malignancy is the best prior art predictor of survival, but the present prognostic is an even better predictor of outcome (see FIG. 7) and accordingly serves as an improved tool for guiding choice of therapy.

As a result of a study performed with respect to a statistically significant sample of 91 human patients, described further below, it was surprisingly found that literally all patients exhibiting an expression level of TGF-α/EGFR levels less than 83/23% of standard survived in excess of five years following standard surgical and radiation treatment for squamous cell head and neck cancer. A surprisingly high percentage of these furthermore survived with "No Evidence of Disease" (NED). These unexpected results in turn allowed the development of a prognostic assay wherein expression levels of either or both of Transforming Growth Factor Alpha (TGF-α) or Epidermal Growth Factor Receptor (EGFR) could be quantitated and normalized as to standard, and the standardized expression level is compared to the prognostic threshold of about 83/23% of standard. Because virtually all if not all patients demonstrating an expression level of 83/23% of standard or less will survive at least five ears after initial diagnosis, assuming standard treatment, such low expression levels of TGF-α and EGFR provide a prognostic indicating good patient prognosis with such standard therapy.

By contrast, and as illustrated vividly by the data summarized in this specification, if the patient demonstrates an expression level of greater than about 83/23% of standard, or the corresponding upper threshold of the "low" tertile regardless of how calculated, the patient can be seen to be in the poor prognosis category, and this information is valuable in guiding choice of therapy. It is not within the scope of the present prognostic assay to delineate actual choice of therapy, because the invention instead provides important information (risk category) to enable appropriate choice of therapy by the skilled practitioner. For purposes of illustration, however, appropriate choice of therapy for patients found to be in the poor prognostic category might include, without limitation, alternative surgical, radiation and/or chemotherapeutic treatments, monoclonal antibody therapy against EGFR such as those used in patients with lung squamous cell carcinoma, or fusion proteins or immunotoxins against TGF-α or EGFR using toxins elaborated by Pseudomonas or Diphtheria species, or other therapies yet to be developed. It is believed that the prognostic threshold identified herein moreover extrapolates to and applies to other cancers besides squamous cell head and neck cancer, based upon the previously documented expression of TGF-α by malignant epithelial cells of virtually or completely all types.

The study which led to the above conclusions was conducted as follows. Archival tissue samples (paraffin embedded) of 91 head and neck squamous cell carcinomas from patients undergoing resection for head and neck cancer from November 1990 to February 1993 were obtained from the diagnostic histopathology laboratories at the University of Pittsburgh Medical Center. Pertinent patient information was abstracted from the medical records. No patient had distant metastasis at the time of tumor resection.

All patients underwent complete surgical resection of the primary tumor with negative surgical margins and 84.6% (77/91) underwent dissection of the cervical lymph nodes with pathologic staging of the regional lymphatics (N-stage). Clinical staging was conducted according to accepted protocols, and clinical follow-up was available for all patients until October, 1996. Patients were classified according to disease status (alive without evidence of disease ("NED"), dead of disease, or dead of other causes). Statistical analysis was performed on the entire patient population.

Diagnosis of squamous cell carcinoma was based on conventional morphologic examination of paraffin-embedded specimens. Staining was performed on tissue sections using monoclonal antibodies specific for TGF-α and EGFR (available from Calbiochem/Oncogene Science and Genosys/Cambridge Research, respectively). A sample of normal skin which demonstrates abundant TGF-α expression was used as a positive control reference standard for TGF-α expression. Cytospins of A431 (a well-characterized vulvar squamous cell carcinoma cell line which over expresses EGFR) provided as slides containing approximately 25,000 cells per slide were fixed in formaldehyde without saponin and were used as a positive control reference standard for EGFR expression. Negative controls for staining consisted of replacement of the primary antibodies with an isotope matched irrelevant murine IgG subclass antibody.

The intensity of immunochemical staining as a reflection of the number of positive granules per cells (mean labeling concentration=mean optical density) was evaluated under 40× magnification on a SAMBA 4000 Image Analysis System (available from Image Products International of Chantilly, Va.) although other optical assessment systems can substitute. Twelve high power fields of each section were analyzed and the result reported as the mean of the optical density (MOD) of the twelve values. The heterogeneity of staining was also determined by computer analysis and reported as concentration heterogeneity which is defined as the concentration variation coefficient between cells and structure (concentration standard deviation/mean concentration). The samples were coded and the pathologists performing the computerized image analysis were blinded to the clinical outcome of the patients. Human skin samples from three different individuals were stained with TGF-α Ab and analyzed on seven separate occasions to assess the variability of this TGF-α standard. Cytospins of A431 cells were stained for EGFR on four different occasions and expression levels were quantitated to determine the variability of the EGFR standard. The raw data from the tumors were analyzed as a percent of the standards (mean optical density) to control for day-to-day staining variability and to ensure that the results could be generalized for prospective data collection in other laboratories. Human skin samples are readily available in most diagnostic pathology laboratories or are available commercially. A431 cells can be obtained, for example, from the American Tissue Culture Collection, 10801 University Boulevard, Manassas, Va. 20110.

Statistical analysis was performed as follows. Survival was measured in months from the date of surgery to the date of death or to the last follow-up. Disease-free survival was defined as the time from resection until the first evidence of recurrence or the development of a new upper aerodigestive tract primary tumor. All surgical resections were considered curative rather than palliative.

Patients were divided into approximately equal tertiles according to TGF-α and EGFR tumor levels for the purpose of generating survival curves. Survivor function curves and median survival times were calculated according to the methods of Kaplan and Meier, which are well known in the art. Confidence intervals for the median were constructed using Greenwood's formula on the log scale. Differences in survivor function due to prognostic factors were calculated by the log-rank test. P values for multiple log rank tests were adjusted with a step-down Bonferroni procedure. The joint effect of predictive variables was evaluated by Cox regression models using continuous variables. Prognostic covariates included in the analysis were sex, age, tumor site, tumor grade, tumor stage, nodal stage, and the mean optical densities of TGF-α and EGFR protein levels in the tumor. Prognostic factors were evaluated individually and all factors having a moderate or strong impact on survival were considered jointly for Cox regression modeling. To assess reliability of the MOD values, repeated measurements of TGF-α and EGFR were obtained in a subset of samples for each marker and the intraclass correlation was estimated.

The results of the testing and statistical analysis were as follows. All 91 head and neck cancer patients studied expressed TGF-α and EGFR protein in their tumors. The SAMBA 4000 Cell Image Analysis System was used to quantify the intensity of immunostaining. For the positive control skin samples, the mean TGF-α MOD for the positive control samples was 19.26+/−0.99. Due to the low variability in the TGF-α and EGFR standards, the raw data (MOD) was analyzed as a percentage of standard for each measurement. Patients whose tumors expressed high levels of TGF-α protein also expressed elevated levels of EGFR (Spearman correlation=0.70, p=0.0001) and they were more likely to have died of disease than patients whose tumors expressed low levels of TGF-α and EGFR (FIG. 4).

On the basis of TGF-α and EGFR protein expression levels, the 91 patients with head and neck squamous cell carcinoma were considered in tertiles and correlated with clinical and pathological parameters. As shown in FIG. 1, gender, age>65, tumor site, tumor stage, nodal stage, or tumor grade were not significantly associated with TGF-α and EGFR protein expression levels in the primary tumor. The association of clinical and pathologic characteristics of head and neck cancer patients with disease-free survival is shown in FIG. 2. In the univariate analysis, the factors with no significant association with decreased disease-free survival were gender, age>65, tumor grade, tumor stage or nodal stage. Tumor site (larynx; p=0.0414) was associated with increased disease-free survival most likely due to both early diagnosis and the relatively sparse lymphatic drainage of the vocal cords. However, the levels of TGF-α (p=0.0001) or EGFR (p=0.0001) protein expressed in the tumor were the strongest predictors of decreased disease-free survival. Disease-free survival was further examined by censoring either recurrences or second primary tumors. TGF-α and EGFR levels were determined to have a significant impact on the recurrence of the index tumor (p=0.001). Although only seven patients developed second primary tumors during the course of the study, both elevated TGF-α (p=0.0111) and EGFR (p=0.0015) levels in the index tumor were associated with the occurrence of a second upper aerodigestive tract malignancy.

Figure 5A:
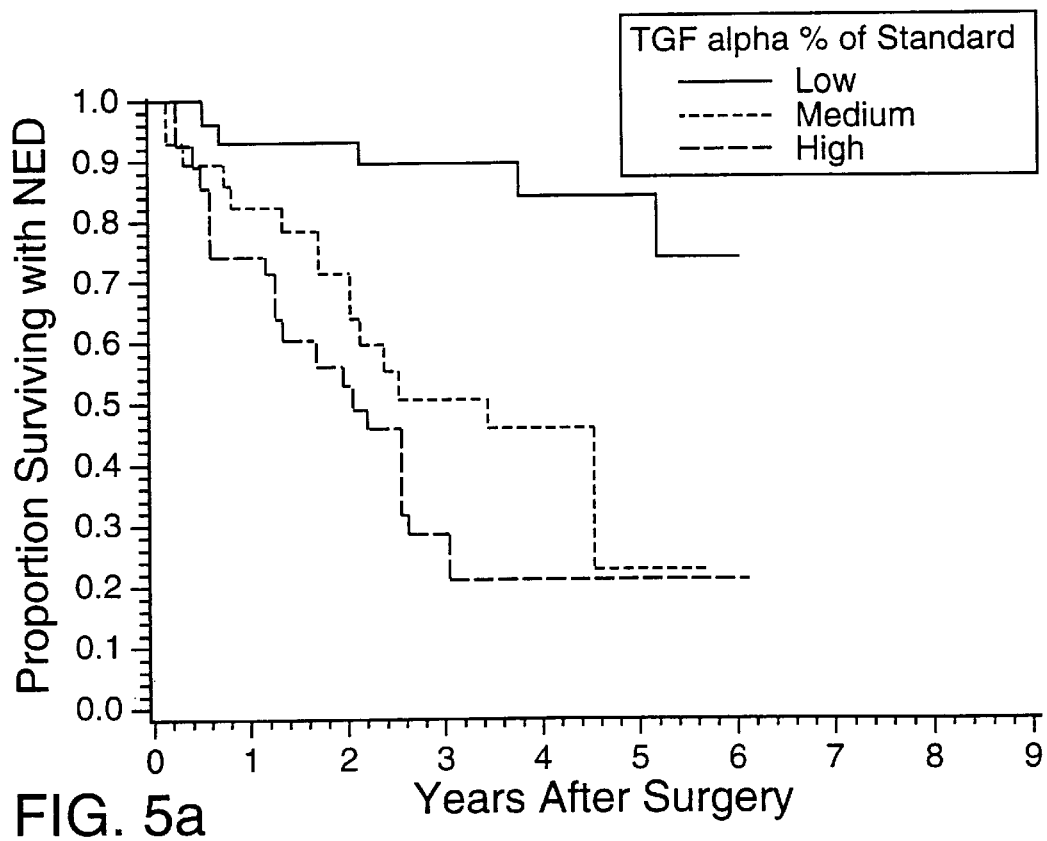
FIGS. 5a and 5b are graphs showing proportion of patients (divided into tertiles) surviving with no evidence of disease, over time.
Figure 5B:
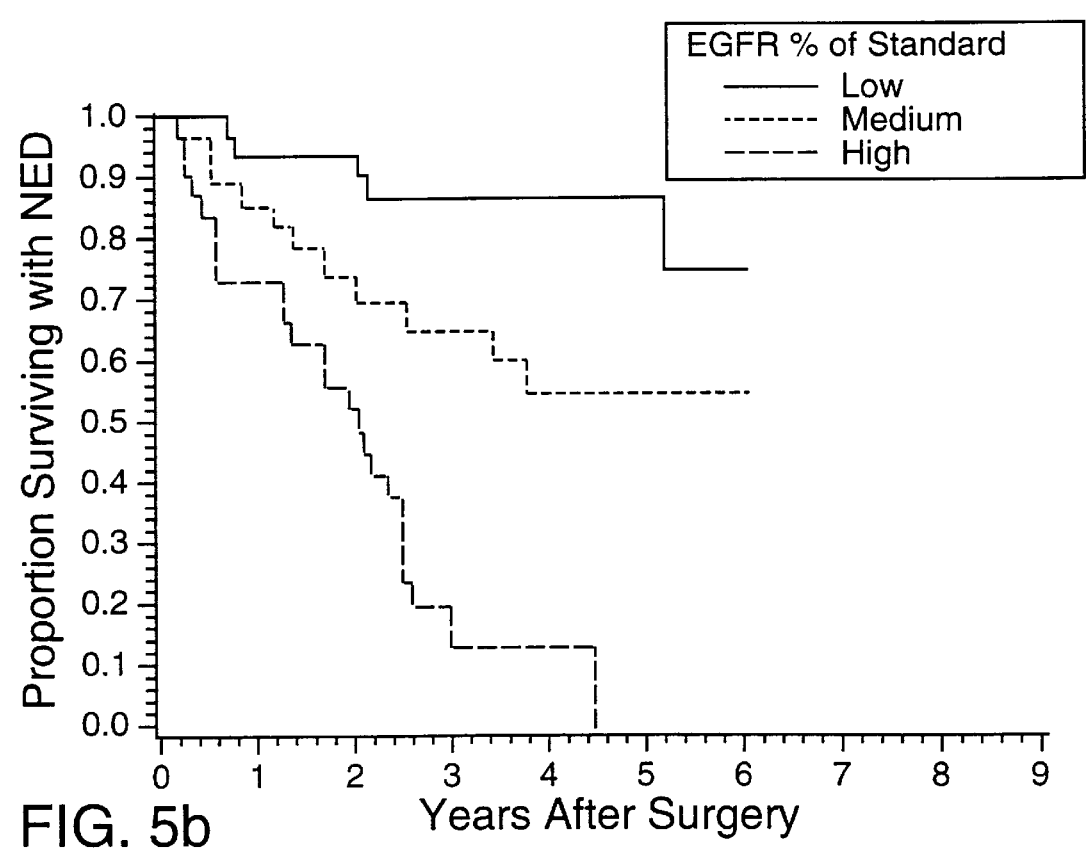
Figure 6A:
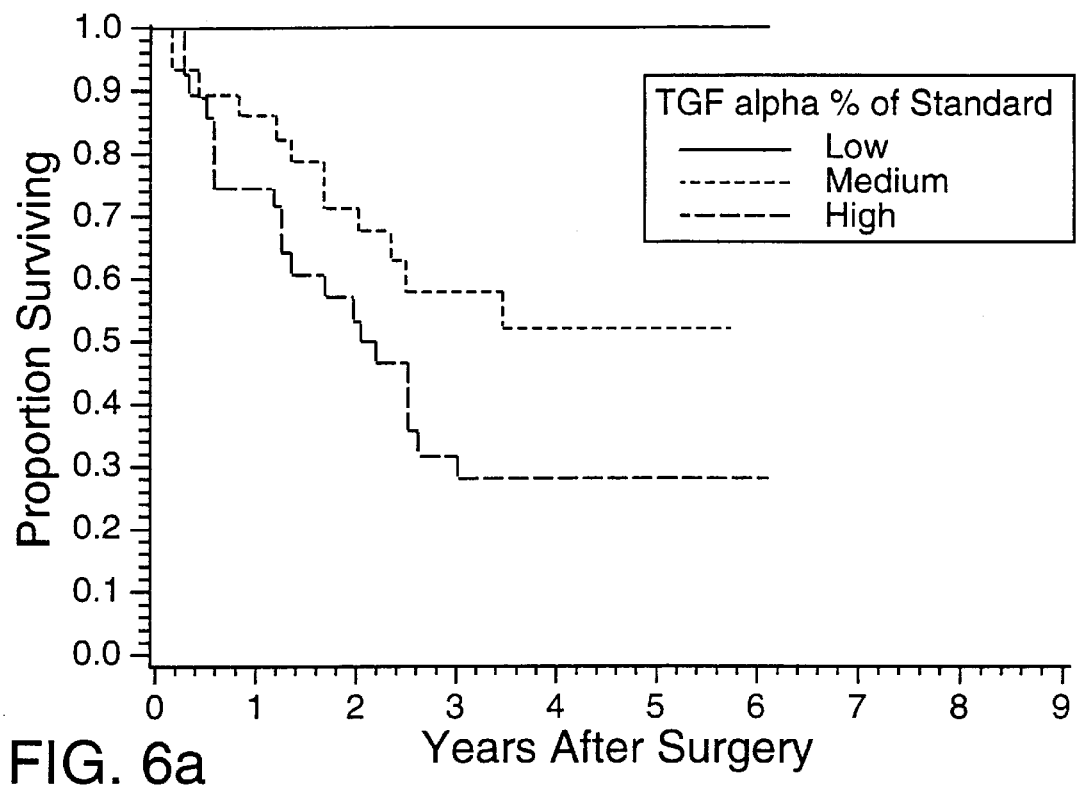
FIGS. 6a and 6b are graphs illustrating overall cause-specific survival proportion over time for the patient tertiles.
Figure 6B:
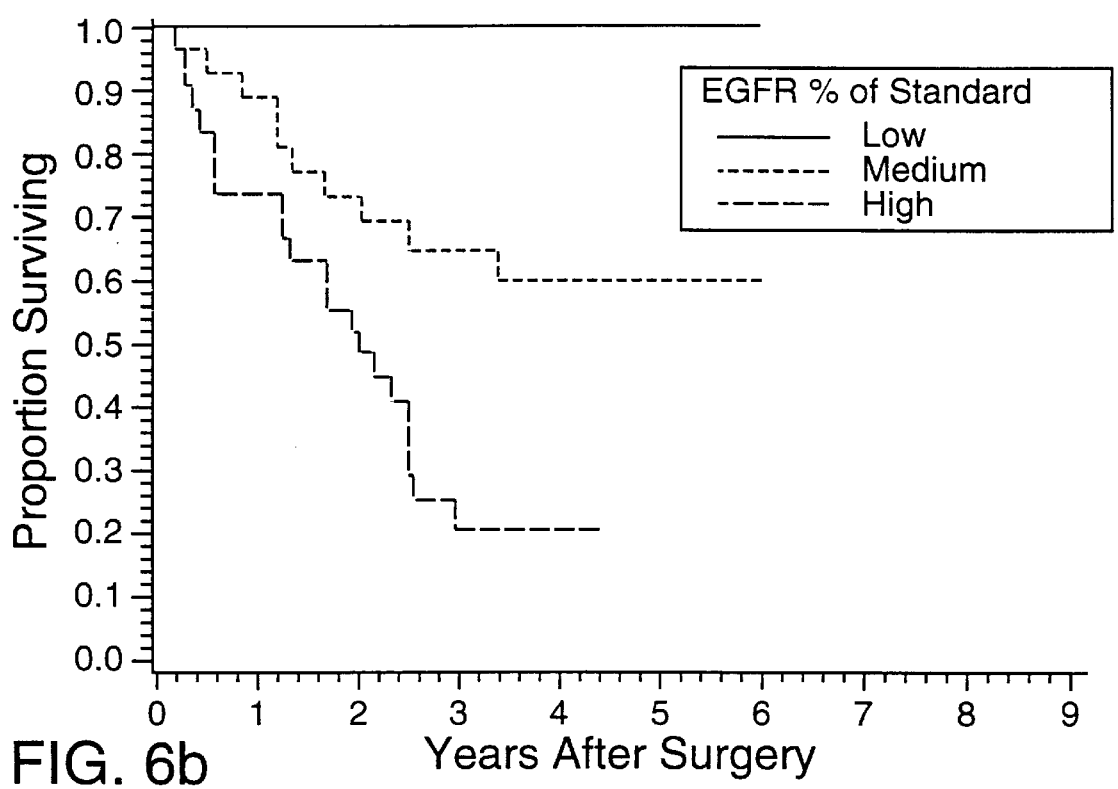
Figure 7A:
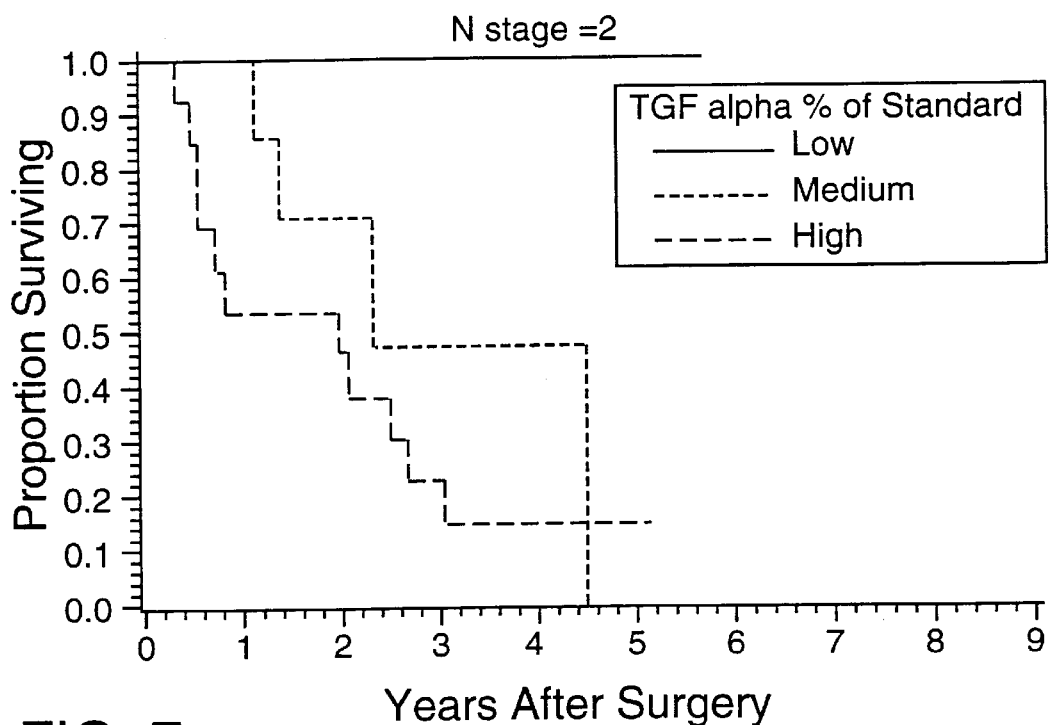
FIGS. 7a, 7b, 7c and 7d are graphs illustrating survival proportion over time for the same patient tertiles divided as to their nodal staging, and further illustrates how the present prognostic changes the way patients are managed vis a vis the use of nodal staging alone.
Figure 7B:
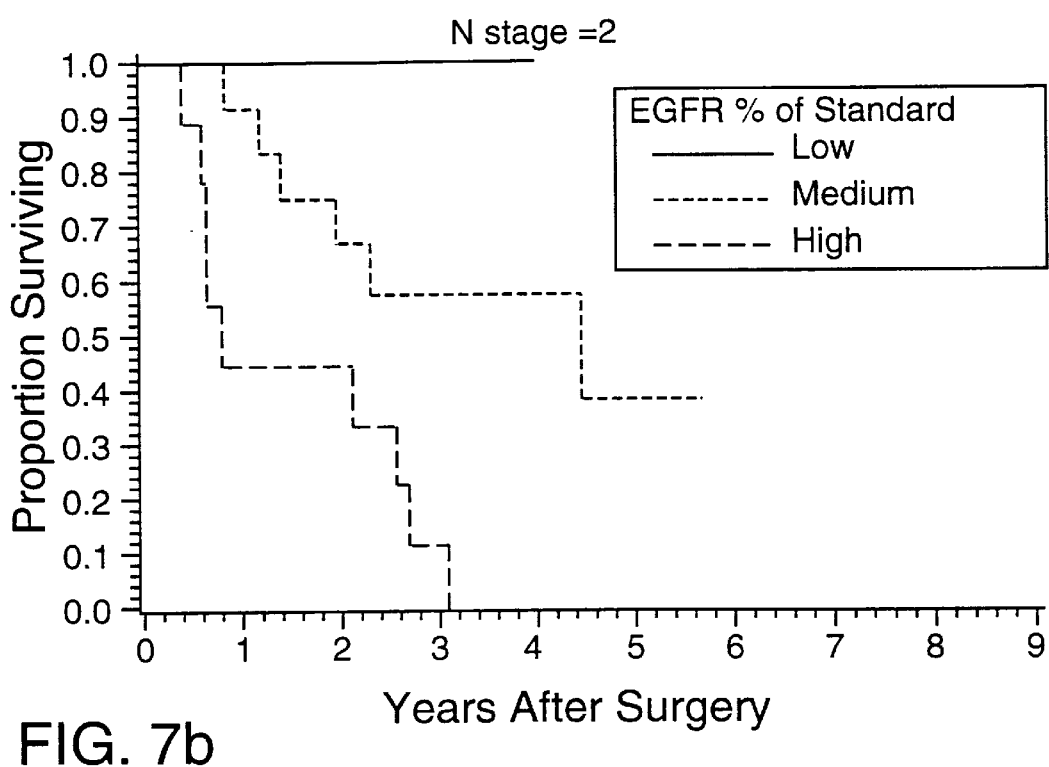
Figure 7C:
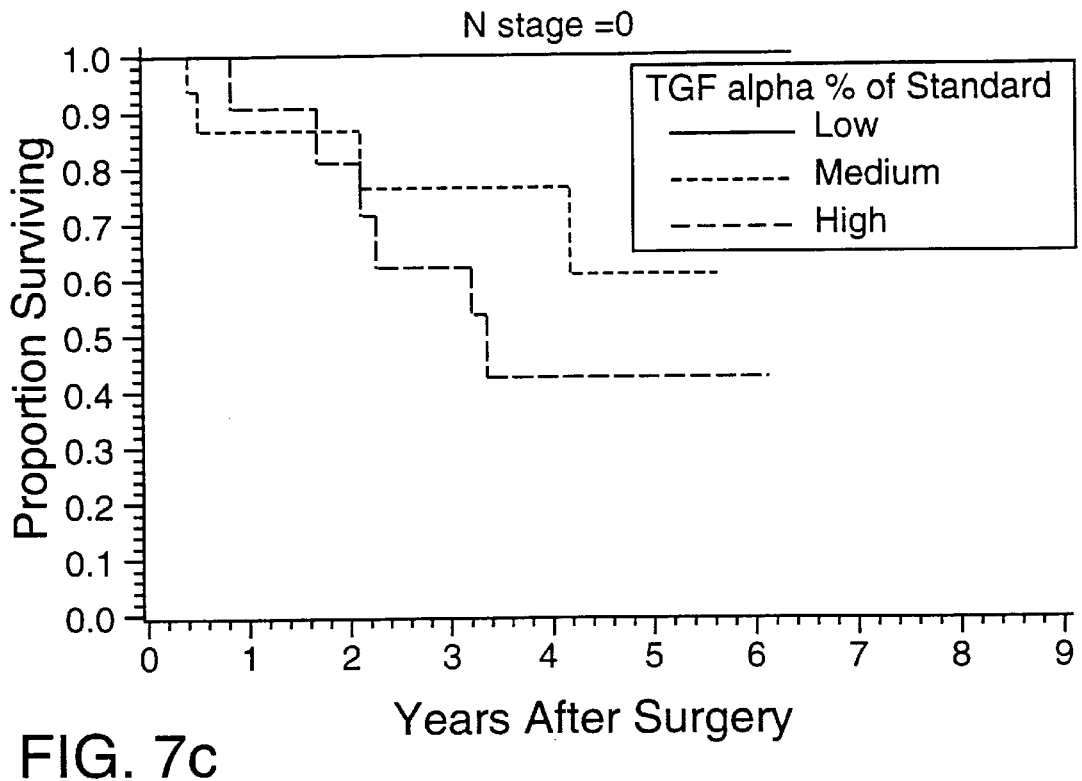
Figure 7D:
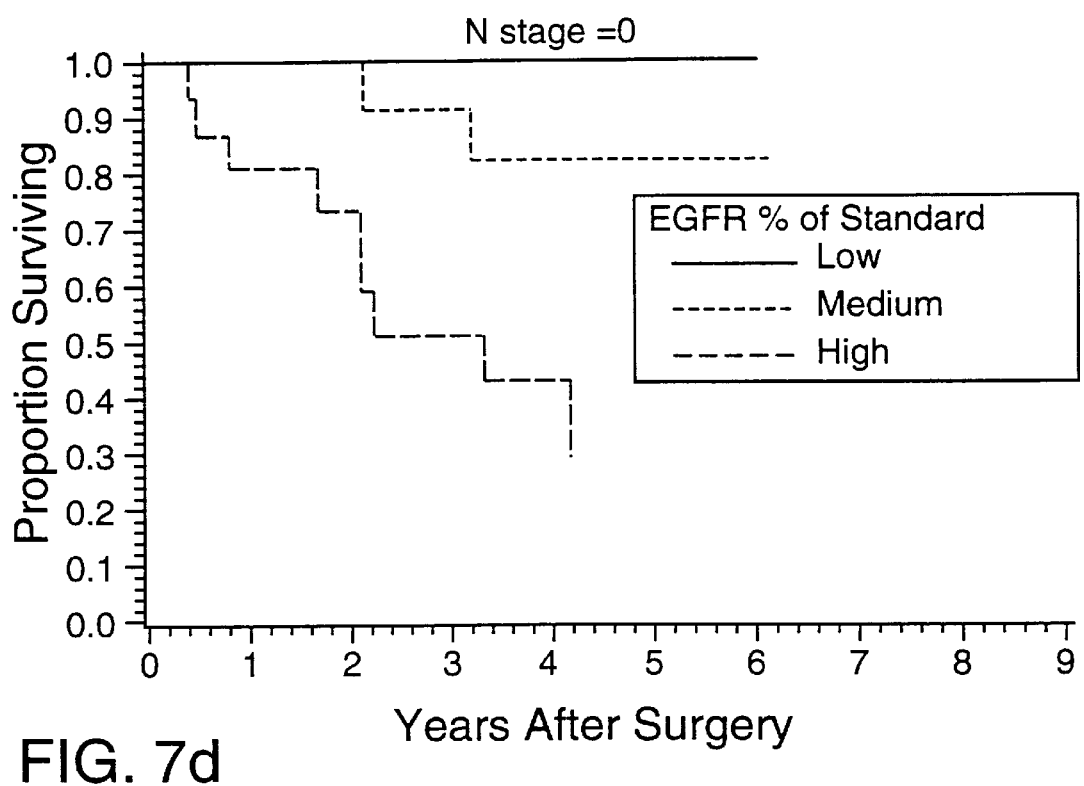

When overall cause-specific survival was examined via univariate analysis, only nodal stage (p=0.0071) TGF-α protein levels (p=0.0001) and EGFR protein levels (p=0.0001) showed significant association with adverse outcome (FIG. 3). Survival curves of patients within each tertile revealed that both TGF-α and EGFR levels in the primary tumor were highly predictive of reduced disease-free ("NED") survival (FIGS. 5a and 5b). Both TGF-α and EGFR levels in the primary tumor were also predictive of reduced overall cause-specific survival when divided into tertiles (FIGS. 6a and 6b). In a Cox regression model, the combination of TGF-α and EGFR levels plus nodal stage was the strongest predictor of survival. The exclusion of EGFR level (p=0.001) from the model resulted in a significant reduction of predictive power. However, the combination of EGFR levels and nodal stage was as strong a predictor of outcome as TGF-α and EGFR levels plus nodal stage (p=0.13; Cox regression overall cause-specific survival; data not shown).

To determine whether TGF-α and EGFR tumor levels predicted survival independent of nodal metastases, tests of interaction were performed which revealed that the effect of TGF-α and EGFR upon overall survival was the same across N-stage categories (FIGS. 7a, 7b, 7c, 7d). TGF-α levels were high (MOD>182% of standard) in 12 patients with no evidence of neck metastases ($N_0$) Six of these twelve patients died of their disease during the course of the study. Similarly, 16 patients with clinicopathologic No staging had high EGFR levels (MOD>100% of standard) in their index tumors, 9 of whom subsequently died of disease. Five patients with advanced disease in their neck ($N_2$) had low TGF-α levels (MOD<83% of standard) in the primary tumor and all are still alive without evidence of disease. EGFR levels were low (MOD<23% of standard) in 4 patients with $N_2$ clinicopathologic staging, all of whom are alive without disease. Conversely, TGF-α tumor levels were low in 18 patients, with No staging, none of whom died of disease and EGFR tumor levels were low in 21 patients with $N_0$ staging all of whom remain alive without evidence of disease. Fourteen patients had high TGF-α tumor levels, 11 of whom died of disease and nine patients had high EGFR tumor levels, all of whom subsequently succumbed to their head and neck cancer. These results surprisingly suggest that TGF-α and EGFR expression levels critically either below about 83/23% of standard or, alternatively, greater than 83/23% of standard, give meaningful prediction of clinical outcome even independently of lymph node status and have significant value in the management of head and neck cancer patients. Because the expression of TGF-α and EGFR has already been documented in other types of malignancies (including bladder, lung, kidney, ovary, brain, cervix, endometrium, esophagus, stomach, pancreas and thyroid), the invention also embraces the method of assessing expression levels according to this important 83/23% of standard threshold, as well.

Expression levels of TGF-α and EGFR mRNA or protein in tissues can be measured by several techniques including radiolabeled ligand binding, Western and Northern blotting, in situ hybridization and quantitative reverse transcription polymerase chain reaction. These molecular techniques, however, are time consuming, requiring a high degree of technical expertise and meticulous processing of the tissue specimen. Also, these techniques are often unable to distinguish the precise cellular source of the molecule(s) under investigation (e.g., tumor cell versus normal epithelial cell versus submucosa). In contrast, immunohistochemistry using commercially available antibodies such as monoclonal antibodies is a standard procedure in all diagnostic pathology laboratories, and can be performed on paraffin-embedded specimens. In the context of the invention, it is both easy and effective to quantify TGF-α and EGFR expression levels in this way. Counting may be manual/optical or standardized optical computer hardware and software may be used, and it was found that even when quantitative image analysis was performed on only a relatively small volume of the tumor tissue, there proved to be a remarkably low level of heterogeneity of either TGF-α or EGFR expression and nothing more was necessary for accurate quantitation.

The easiest way to visualize the criticality of the about <83/23% of standard expression levels of the present invention is to compare FIGS. 5–7 as follows. The "low" expression group in each graph represents the tertile of patients for whom expression levels were lower than about 83/23% of standard. In all but FIGS. 5a and 5b, the data show lines for the "low" group straight across on the "proportion surviving" axis, i.e., no deaths. Even in FIGS. 5a and 5b, this same group still had no deaths for at least five years, and the only reason the curve for this group declined somewhat is that a relatively small proportion of this did have some evidence of disease. The "flat lines" of FIGS. 7a, b, c and d therefore indicate surprising and unexpected results—the expression levels of the present invention are by no means a smooth continuum, but in fact can be seen pictorially to have a critical level with prognostic meaning both above and below. It is the use of this critical level as a threshold, in an otherwise standard laboratory assay thus given entirely new utility, which forms the heart of the present invention, The alternative way to visualize the unexpected results attributable to the present unexpectedly critical expression threshold is apparent in FIG. 4. The solid black dots represent deaths from squamous cell head and neck cancer; the stars represent survivors of squamous cell head and neck cancer, and the hollow dots represent deaths from other causes (traffic accidents, etc.), all from the same study of 91 patients. As can be seen dramatically from FIG. 4, the solid black dots representing deaths cluster within a neat and easily definable sector with respect to elevated TGF-α and EGFR levels, as likewise do the survivor stars. As to the "death" dots, there are not even any statistical "outlyers," which never could have been predicted.

Although the invention has been described with particularity above, with respect to particular methods and patient populations, the invention is only to be limited insofar as is set forth in the accompanying claims.

What is claimed is:

1. A prognostic method to predict the survival of a patient already diagnosed to have a malignancy, comprising the steps of:

a) obtaining a sample of malignant cells from a patient;

b) quantifying expression of a protein selected from the group consisting of Transforming Growth Factor Aloha (TGF-α) and Epidermal Growth Factor Receptor (EGFR) in said sample;

c) normalizing the values quantitated in step b) as to standard, to yield a normalized percentage expression as to standard; and d) assessing whether said normalized percentage expression as to standard falls into the poor or good prognostic category as determined by calculable survival curves by assessing whether said normalized percentage expression as to standard falls into a good prognosis category of less than about 83% of standard for TGF-α or falls into a good prognosis category of less than about 23% of standard for EGFR, wherein the assessment performed in step d) has prognostic significance in predicting patient survival.

2. The method according to claim 1 wherein said malignant cells are selected from the group consisting of squamous cell head and neck cancer cells, bladder cancer cells, lung cancer cells, kidney cancer cells, ovarian cancer cells, brain cancer cells, cervical cancer cells, endometrial cancer cells, esophageal cancer cells, stomach cancer cells, pancreatic cancer cells, and thyroid cancer cells.

3. The method according to claim 1 wherein said malignant cells are squamous cell head and neck cancer cells.

4. The method according to claim 1 wherein said quantifying is conducted by contacting said malignant cells with monoclonal antibodies specific to TGF-α or EGFR and further quantifying the resulting binding to assess the presence of TGF-α or EGFR.

5. The method according to claim 4 wherein said quantifying is conducted on a laboratory slide.

6. The method according to claim 5 wherein said quantifying is conducted optically, by eye.

7. The method according to claim 5 wherein said quantifying is conducted automatically, using image analysis hardware and software.

8. The method according to claim 5, wherein the results of step d) are considered in association with nodal staging of the patient.

* * * * *

UNITED STATES PATENT AND TRADEMARK OFFICE
CERTIFICATE OF CORRECTION

PATENT NO.   : 6,063,586  
DATED        : May 16, 2000  
INVENTOR(S)  : Jennifer Rubin Grandis Page 1 of 1

It is certified that error appears in the above-identified patent and that said Letters Patent is hereby corrected as shown below:

<u>Title page,</u>
Item [75] insert -- Mona F. Melhem, Pittsburgh, Pa. --

<u>Column 6,</u>
Line 45, after "($N_o$)" insert -- . --.
Line 47, "No" should read -- $N_o$ --.
Line 56, "No" should read -- $N_o$ --.

<u>Column 7,</u>
Line 11, "in situ" should read -- *in situ* --.

<u>Column 8,</u>
Line 17, claim 1, "Aloha" should read -- Alpha --.

Signed and Sealed this

Fourth Day of September, 2001

*Attest:*

NICHOLAS P. GODICI
*Attesting Officer*    *Acting Director of the United States Patent and Trademark Office*